US011633368B2

(12) United States Patent
Moore

(10) Patent No.: US 11,633,368 B2
(45) Date of Patent: Apr. 25, 2023

(54) ENHANCED MOISTURIZING LOTION COMPOSITIONS

(71) Applicant: Milton D. Moore, Pearland, TX (US)

(72) Inventor: Milton D. Moore, Pearland, TX (US)

(73) Assignee: Milton D. Moore, Pearland, TX (US)

( * ) Notice: Subject to any disclaimer, the term of this patent is extended or adjusted under 35 U.S.C. 154(b) by 0 days.

(21) Appl. No.: 17/010,123

(22) Filed: Sep. 2, 2020

(65) Prior Publication Data

US 2021/0059958 A1     Mar. 4, 2021

Related U.S. Application Data

(60) Provisional application No. 62/994,155, filed on Mar. 24, 2020, provisional application No. 62/895,037, filed on Sep. 3, 2019.

(51) Int. Cl.

| | |
|---|---|
| *A61K 31/047* | (2006.01) |
| *A61K 36/886* | (2006.01) |
| *A61K 36/76* | (2006.01) |
| *A61K 36/28* | (2006.01) |
| *A61K 31/17* | (2006.01) |
| *A61K 31/27* | (2006.01) |
| *A61K 8/34* | (2006.01) |
| *A61K 8/41* | (2006.01) |
| *A61K 8/97* | (2017.01) |
| *A61K 8/92* | (2006.01) |
| *A61Q 19/00* | (2006.01) |
| *A61P 17/04* | (2006.01) |
| *A61K 31/05* | (2006.01) |

(52) U.S. Cl.
CPC ............ *A61K 31/047* (2013.01); *A61K 8/345* (2013.01); *A61K 8/347* (2013.01); *A61K 8/41* (2013.01); *A61K 8/922* (2013.01); *A61K 8/97* (2013.01); *A61K 31/05* (2013.01); *A61K 31/17* (2013.01); *A61K 31/27* (2013.01); *A61K 36/28* (2013.01); *A61K 36/76* (2013.01); *A61K 36/886* (2013.01); *A61P 17/04* (2018.01); *A61Q 19/007* (2013.01); *A61K 2800/884* (2013.01)

(58) Field of Classification Search
None
See application file for complete search history.

(56) References Cited

U.S. PATENT DOCUMENTS

| | | |
|---|---|---|
| 4,709,481 A | 12/1987 | Moore |
| 4,944,939 A | 7/1990 | Moore |
| 5,387,412 A | 2/1995 | Moore |
| 6,861,051 B2 | 3/2005 | Moore |
| 9,717,659 B2 | 8/2017 | Botello et al. |
| 9,795,550 B2 | 10/2017 | Hood et al. |
| 2009/0047226 A1 | 2/2009 | Teckenbrock et al. |
| 2009/0050170 A1 | 2/2009 | Moore |
| 2009/0123409 A1 | 5/2009 | Moore |
| 2017/0042784 A1 | 2/2017 | Munk et al. |
| 2017/0333346 A1 | 11/2017 | Burnam |
| 2018/0042840 A1 | 2/2018 | Alminana et al. |

FOREIGN PATENT DOCUMENTS

| | | | |
|---|---|---|---|
| CN | 105125467 A | * | 12/2015 |
| CN | 109568246 A | * | 4/2019 |

OTHER PUBLICATIONS https://en.wikipedia.org/wiki/Verbena—accessed Nov. 2021.*
https://www.merriam-webster.com/thesaurus/lotion—accessed Nov. 2021.*
Singh (Pharmacognosy Reviews (2011), vol. 5, No. 9, pp. 82-95).*

\* cited by examiner

*Primary Examiner* — Susan Hoffman
(74) *Attorney, Agent, or Firm* — Conley Rose, P.C.

(57) ABSTRACT

A moisturizing lotion composition includes water. In addition, the moisturizing lotion composition includes propylene glycol having a concentration of 21.0 to 37.5 wt % of the moisturizing lotion composition. Further, the moisturizing lotion composition includes aloe vera having a concentration of 0.50 to 4.0 wt % of the moisturizing lotion composition. Still further, the moisturizing lotion composition includes vervain extract having a concentration of 0.50 to 4.0 wt % of the moisturizing lotion composition. Moreover, the moisturizing lotion composition includes willow bark extract having a concentration of 0.50 to 0.20 wt % of the moisturizing lotion composition. The moisturizing lotion composition also includes chamomilla recutita extract having a concentration of 0.05 to 0.40 wt % of the moisturizing lotion composition.

22 Claims, No Drawings

ENHANCED MOISTURIZING LOTION COMPOSITIONS

CROSS-REFERENCE TO RELATED APPLICATIONS

This application claims benefit of U.S. provisional patent application Ser. No. 62/895,037 filed Sep. 3, 2019, and entitled "ENHANCED MOISTURIZING LOTION COMPOSITIONS," and U.S. provisional patent application Ser. No. 62/994,155 filed Mar. 24, 2020, and entitled "ENHANCED MOISTURIZING LOTION COMPOSITIONS," each of which is hereby incorporated herein by reference in their entireties for all purposes.

STATEMENT REGARDING FEDERALLY SPONSORED RESEARCH OR DEVELOPMENT

Not applicable.

BACKGROUND

Embodiments disclosed herein relate generally to topical moisturizing lotions. More specifically, embodiments disclosed herein relate to topical moisturizing lotions for treating skin irritation, inflammation, and discomfort.

Many individual suffer from chronic or acute skin irritation, inflammation, or discomfort Such symptoms may be due to a variety of causes including preexisting skin disorders or diseases (e.g., eczema), exposure to a particular substance (e.g., a poisonous compound, certain chemicals in beauty products, poison ivy, etc.), insect bites, etc. The spectrum of resulting symptoms can as minor as some localized redness to extreme pain and discomfort.

BRIEF SUMMARY

Embodiments of moisturizing lotion composition are disclosed herein. In one embodiment, a moisturizing lotion composition comprises water. In addition, the moisturizing lotion composition comprises propylene glycol having a concentration of 21.0 to 37.5 wt % of the moisturizing lotion composition. Further, the moisturizing lotion composition comprises aloe vera having a concentration of 0.50 to 4.0 wt % of the moisturizing lotion composition. Still further, the moisturizing lotion composition comprises vervain extract having a concentration of 0.50 to 4.0 wt % of the moisturizing lotion composition. Moreover, the moisturizing lotion composition comprises willow bark extract having a concentration of 0.50 to 0.20 wt % of the moisturizing lotion composition. The moisturizing lotion composition also comprises chamomilla recutita extract having a concentration of 0.05 to 0.40 wt % of the moisturizing lotion composition.

In another embodiment, a moisturizing lotion composition comprises de-ionized water. In addition, the moisturizing lotion composition comprises propylene glycol having a concentration of 12.5 to 50.0 wt % of the moisturizing lotion composition. Further, the moisturizing lotion composition comprises aloe vera having a concentration of 0.5 to 2.0 wt % of the moisturizing lotion composition. Still further, the moisturizing lotion composition comprises vervain extract having a concentration of 0.50 to 4.0 wt % of the moisturizing lotion composition. Moreover, the moisturizing lotion composition comprises chamomilla recutita extract having a concentration of 0.07 to 1.5 wt % of the moisturizing lotion composition. The moisturizing lotion composition also comprises panthenol having a concentration of 0.25 to 2.0 wt % of the moisturizing lotion composition. Further, the moisturizing lotion composition comprises willow bark extract having a concentration of 0.09 to 0.13 wt % of the moisturizing lotion composition. A ratio of the concentration of the aloe vera to the concentration of the vervain extract is between 0.90 and 1.10. A ratio of the concentration of the propylene glyocol to the concentration of the panthenol is between 45.0 and 55.0.

Embodiments of methods for treating skin are disclosed herein. In one embodiment, a method for treating skin comprises (a) applying a moisturizing lotion composition to the skin. The moisturizing lotion composition comprises water. In addition, the moisturizing lotion composition comprises propylene glycol having a concentration of 21.0 to 37.5 wt % of the moisturizing lotion composition. Further, the moisturizing lotion composition comprises aloe vera having a concentration of 0.50 to 4.0 wt % of the moisturizing lotion composition. Still further, the moisturizing lotion composition comprises vervain extract having a concentration of 0.50 to 4.0 wt % of the moisturizing lotion composition. Moreover, the moisturizing lotion composition comprises willow bark extract having a concentration of 0.50 to 0.20 wt % of the moisturizing lotion composition. The moisturizing lotion composition also comprises chamomilla recutita extract having a concentration of 0.05 to 0.40 wt % of the moisturizing lotion composition. The method further comprises (b) applying a secondary compound to the skin. The secondary compound comprises an antimicrobial.

Embodiments described herein comprise a combination of features and characteristics intended to address various shortcomings associated with certain prior compositions and methods. The foregoing has outlined rather broadly the features and technical characteristics of the disclosed embodiments in order that the detailed description that follows may be better understood. The various characteristics and features described above, as well as others, will be readily apparent to those skilled in the art upon reading the following detailed description and examples. It should be appreciated that the conception and the specific embodiments disclosed may be readily utilized as a basis for modifying or designing other compositions and methods for carrying out the same purposes as the disclosed embodiments. It should also be realized that such equivalent constructions do not depart from the spirit and scope of the principles disclosed herein.

DETAILED DESCRIPTION

The following discussion is directed to various exemplary embodiments. However, one of ordinary skill in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function.

In the following discussion and in the claims, the terms "including" and "comprising" are used in an open-ended fashion, and thus should be interpreted to mean "including, but not limited to . . . " In addition, as used herein "applying" may include any method of introducing a composition or substance into contact with the skin, such as by being rubbed, poured, sprinkled, sprayed, or combinations thereof. Further, as used herein, a "cosmetic use" includes any use intended to improve the aesthetic appearance of the skin, such as by cleansing, beautifying, promoting attractiveness, or combinations thereof. A cosmetic benefit is typically visual or aesthetic, and can be evaluated using subjective and/or objective assays known in the art. As used herein, a "dermopharmaceutical use" includes uses intended for the treatment, mitigation or prevention of a disease or disorder of the skin, and/or intended to affect the structure or a function of the skin. A dermopharmaceutical use typically has a physiological, pharmacological, and/or therapeutic effect on the skin. A dermopharmaceutical use may result in an improved aesthetic appearance of the skin by virtue of its physiological, pharmacological, or therapeutic effects. A dermopharmaceutical benefit can be evaluated using subjective and/or objective assays known in the art. As used herein, an "antimicrobial use" is a use that targets, kills, inactivates, or slows the growth of microorganisms, and thus is defined broadly herein to include antibiotic uses, antibacterial uses, antiviral uses, and antiseptics uses. In general, antibiotic uses are those that target and/or kill bacteria, fungi, parasites, or combinations thereof. Antibacterial uses are those that target and/or kill bacterial cells, and may rely on a bacteriocidal that deteriorates the integrity of cell walls and/or a bacteriostatic that inhibits the growth and/or reproduction of bacterial cells. Antiviral uses are those that kill viruses, inhibit the growth of viruses, or otherwise target viruses. Antiseptics are substances typically used on bodily tissues (e.g., skin) to reduce the possibility of infections, sepsis, or putrefaction, and are generally distinguished from antibiotics, which are internally transportable via the lymphatic system within the body. Thus, antimicrobial uses may include the use of compounds usable outside of the body only (e.g., on the face or hands), uses within the body (e.g., within the nasal passages, mucous membranes), and uses that may or may not involve compounds transportable via the lymphatic system. As described in more detail below, coronaviruses are a group of related viruses defined broadly to include, for example: Severe Acute Respiratory Syndrome Coronavirus 2 (SARS-CoV-2), cause of Coronavirus Disease 2019 (COVID-19); Severe Acute Respiratory Syndrome virus (SARS-CoV), cause of Severe Acute Respiratory Syndrome (SARS); and Middle East Respiratory Syndrome Coronavirus (MERS-CoV), cause of the Middle East Respiratory Syndrome (MERS), and Human Coronaviruses (HCoVs)]. It should be appreciated that recent research suggests that coronaviruses, including SARS-CoV-2, SARS-CoV, MERS-CoV, and HCoVs can persist on inanimate surfaces like metal, glass, or plastic for up to 9 days, but can be efficiently inactivated within one minute in response to contact with surface disinfectant comprising, for example, 62% to 71% ethanol, 0.5% hydrogen peroxide or 0.1% sodium hypochlorite, as described for example in Persistence of Coronaviruses on Inanimate Surfaces and Their Inactivation With Biocidal Agents by G. Kampf et al. Journal of Hospital Infection, Volume 104, Issue 3, March 2020, Pages 246-251, which is hereby incorporated herein by reference in its entirety. As used herein, a "dermal delivery" refers to a process of mass transport of active ingredients applied on the skin to various skin strata. In comparison, as used herein a "transdermal delivery" refers to the entire process of mass transport of substances applied on the skin surface and includes their absorption by each skin strata, the strata's uptake by microcirculation, and the further distribution in the outer systemic circulation to at least a minor degree. As used herein, the term "antimicrobial" refers to an agent that kills or prohibits the growth of microorganisms such as bacteria, fungals, viruses, and parasites. Thus, antimicrobials include antibacterials (e.g., bactericides), antivirals, antiparasitics, and antifungals.

As used herein, the terms "approximately," "about," "substantially," and the like mean within 10% (i.e., plus or minus 10%) of the recited value. Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

Embodiments of compositions and methods for using same as disclosed herein may be used for cosmetic uses, dermopharmaceutical uses, antimicrobial uses, or combinations thereof. Such compositions may generally be referred to herein as "moisturizing lotion compositions," which can be used to treat the skin, protect the skin, improve the condition of the skin, improve the aesthetic appearance of skin, or combinations thereof.

In general, embodiments of compositions disclosed herein (e.g., moisturizing lotion compositions) may be suitable for use on skin to moisturize, hydrate, reduce inflammation, reduce irritation, reduce pain, or combinations thereof. For example, the properties of embodiments of moisturizing lotion compositions disclosed herein may be particularly beneficial for treating eczema, psoriasis, rosacea, or dermatitis including: contact dermatitis, photo dermatitis, seborrheic dermatitis, nummular dermatitis, stasis dermatitis, dermatitis herpetiformis, atopic dermatitis, and allergic dermatitis. According to some embodiments, the moisturizing lotion compositions disclosed herein is suitable for treating diabetic neuropathy and reducing nerve pain of the skin. For example, some embodiments of compositions disclosed herein contain combinations of compounds that exhibit analgesic (e.g., pain relieving) benefits that are enhanced by a dermal or transdermal delivery behavior of the compositions, which offers the potential to increase the degree of pain relief and/or reduce the time to achieve such pain relief. In some testing described in more detail below, the onset of pain relief following application of embodiments of moisturizing lotions described herein resulted in less than 5 minutes of application. In addition, the moisturizing and/or hydration properties of some embodiments of compositions disclosed herein offer the potential to reduce sagging, reduce scarring, reduce age spots, reduce wrinkles, or combinations thereof. Similarly, some embodiments of compositions disclosed herein may be beneficial for treating skin damage and/or irritation associated with chafing, sunburn, sensitive skin, dry skin, rough skin, flaky skin, red skin, irritated skin, and itchy skin. In other instances, the anti-inflammatory properties of embodiments disclosed herein may improve acne, blisters, rash, or hives.

Embodiments of moisturizing lotion compositions will now be described. Such moisturizing lotion compositions include a plurality of compounds or ingredients that are uniformly and homogeneously blended together to offer potential for synergistic benefits in treating the skin. More specifically, embodiments of moisturizing lotion compositions disclosed herein include one or more of the following: skin conditioning agent(s), aloe vera, algae extract, vervain extract, an anti-inflammatory agent, cationic polymer(s), film forming barrier(s), emollient(s), cationic low humidity humectant(s), willow bark extract, antifungal and/or antibacterial compound(s), cetyl alcohol, surfactant(s) and/or emulsion agent(s), anti-wrinkle agent(s), alpha hydroxyl acid(s), lipid(s) and/or monoglyceride(s), and anti-oxidant agent(s). One or more of the foregoing ingredients are mixed in a solvent, and in particular water, to form an aqueous solution. In some embodiments, a fragrance may also be added.

Embodiments of the moisturizing lotion composition can include a variety of types of skin conditioning agents including, without limitation, propylene glycol. In such embodiments, the propylene glycol has a concentration (expressed as a wt % of the moisturizing lotion composition) ranging from about 12.5 wt % to about 40.0 wt %, alternatively ranging from about 18.7 wt % to about 37.5 wt % of the moisturizing lotion composition, alternatively ranging from about 21.0 wt % to 37.5 wt % of the moisturizing lotion composition, and alternatively from about 22.5% to about 31.3% wt % of the moisturizing lotion composition. The skin conditioning agent (e.g., propylene glycol) acts as a dermal and/or transdermal delivery agent, thereby assisting with and facilitating penetration of the skin.

Other skin conditioning agent(s) such as chamomilla recutita extract may be used alone or in combination with propylene glycol. In such embodiments, the chamomilla recutita extract has a concentration (expressed as a wt % of the moisturizing lotion composition) ranging from about 0.05 wt % to about 0.40 wt %, alternatively ranging from about 0.07 wt % to about 0.15 wt %, and alternatively ranging from about 0.09 wt % to about 0.13 wt %.

Chamomilla recutita extract functions as a skin conditioning agent by moisturizing the skin and restoring suppleness. In addition, chamomilla recutita extract is an antioxidant that protects skin from free-radical damage.

Chamomilla recutita extract also provides antiseptic and anti-inflammatory properties. Such properties can aid in fading spots on the skin, eliminating scars, and treating acne. In addition, chamomilla recutita extract can provide analgesic (e.g., pain relieving) benefits as described in Clinical Evaluation of Fluid Extract of Chamomilla Recutita for Oral Aphthae, M. Ramos et al., Journal of Drugs Dermatol. 2006; 5(7):612-617, which is hereby incorporated herein by reference in its entirety. Further, flavinoids in chamomilla recutita extract can sooth and calm the skin, and offer the potential to improve the speed at which damaged skin heals. Accordingly, chamomilla recutita extract may be particularly beneficial in treating dry skin, eczema, psoriasis, and skin irritation. Chamomilla recutita extract may also be particularly beneficial for with particularly sensitive skin as it is anti-irritating, non-comedogenic, and hypoallergenic.

In embodiments described in more detail below where the moisturizing lotion composition is used to enhance the antimicrobial efficacy of secondary compounds applied to the skin, the chamomilla recutita extract may work in combination with the panthenol, aloe vera, and salicylic acid to further sooth skin irritation and further increase the antimicrobial efficacy of such secondary compounds.

Embodiments of the moisturizing lotion composition can include aloe vera such as aloe barbadensis, aloe barbadensis leaf juice, aloe vera gel, aloe vera extract, or combinations thereof. In such embodiments, the aloe vera has a concentration (expressed as a wt % of the moisturizing lotion composition) ranging from about 0.50 wt % to about 4.00 wt %, alternatively ranging from about 0.75 wt % to about 1.50 wt %, and alternatively ranging from about 0.90 wt % to about 1.25 wt %.

The aloe vera is an anti-inflammatory and provides analgesic (i.e., pain relieving) effects. The aloe vera also provides skin calming (soothing and cooling), moisturizing, and anti-wrinkle properties. Consequently, aloe vera may be particularly beneficial for treating burns, eczema, and related irritation and pain. Such benefits may be enhanced by improved dermal and/or transdermal delivery properties of the moisturizing lotion composition.

In embodiments described in more detail below in which the moisturizing lotion composition is used to enhance the antimicrobial efficacy of one or more secondary compounds applied to the skin, the aloe vera may sooth or otherwise mitigate skin irritation, thereby allowing higher concentrations of antimicrobial agents to be applied to sensitive skin areas as compared to skin that has not been treated with the moisturizing lotion composition. Thus, for instance, application of the moisturizing lotion composition may enable hand sanitizers with higher concentrations of alcohol to be applied to skin, face, or nasal passages when the moisturizing lotion composition is applied to such areas in combination with the sanitizer (e.g., before, simultaneous with, or after application of the sanitizer). Similarly, the aloe vera prolong the period of time the skin can be exposed to such secondary compounds. As a result, the enhancements to the antimicrobial efficacy of such secondary compounds provided by aloe vera may be two-fold, as the short term effectiveness may be increased by the higher concentrations of antimicrobial agents (e.g. alcohol, etc.), and the long term effectiveness may be increased as the antimicrobial agents may remain on the skin for a longer period of time.

Embodiments of the moisturizing lotion composition can include algae extract derived or extracted from a variety of sources including, without limitation, freshwater algae species such as green algae, red algae, brown algae, or combinations thereof; seaweed; marine algae (e.g., kelp extracts such as alginate); cyanobacteria or "blue-green algae;" and combinations thereof. In embodiments described herein, red or brown algae extract are particularly preferred. The algae extract has a concentration (expressed as a wt % of the moisturizing lotion composition) ranging from about 1.0 wt % to 8.0 wt %, alternatively ranging from about 1.5 wt % to about 3.0 wt %, and alternatively ranging from about 1.8 wt % to about 2.5 wt %.

The algae extract functions as an antioxidant, moisturizes the skin, normalizes the moisture content of the skin, and provides suppleness, which can result in anti-aging characteristics. In addition, the algae extract provides lubrication and hydration to the skin. Algae extract is a non-irritating and noncomedogenic. Accordingly, embodiments of the moisturizing lotion compositions including algae extract offer the potential to provide improved modes and rates for hydration and lubrication, as well as delivery of other ingredients of the moisturizing lotion composition into the epidermis. The algae extract may also provide analgesic (e.g., pain relieving) benefits and/or facilitate analgesic benefits provided by other constituents of the moisturizing lotion composition.

Embodiments of the moisturizing lotion composition can include vervain extract. In such embodiments, the vervain extract included in the moisturizing lotion composition has a concentration (expressed as a wt % of the moisturizing lotion composition) ranging from about 0.50 wt % to about 4.00 wt %, alternatively ranging from about 0.75 wt % to about 1.50 wt %, and alternatively ranging from about 0.90 wt % to about 1.25 wt %.

Vervain extract is an anti-oxidant, which may work in synergy with essential derivatives to beneficially scavenge free radicals. The vervain extract may also enhance prostaglandins, which stimulates extracellular transmission of the active ingredients of the moisturizing lotion composition. In addition, vervain extract may provide analgesic (e.g., pain relieving) benefits, as well as function as a skin conditioning agent with emollient properties. Without being limited by any theory, vervain extract is also believed to stimulate circulation as an arterial vasodilator and as a decongestive on vein flow, which may enhance the rate of dispersion of one or more of the ingredients of the moisturizing lotion composition and/or enhance the rate of pain relief.

Embodiments of the moisturizing lotion composition can include one or more anti-inflammatory agents including, without limitation, panthenol. In embodiments including panthenol as an anti-inflammatory agent, the panthenol has a concentration (expressed as a wt % of the moisturizing lotion composition) ranging from about 0.25 wt % to about 2.00 wt %, alternatively ranging from about 0.37 wt % to about 0.75 wt %, and alternatively ranging from about 0.45 wt % to about 0.63 wt %. The anti-inflamatory agent(s) such as panthenol offer the potential to reduce redness and irritation of the skin, while also supplementing the moisturizing and lubricity of the moisturizing lotion composition.

As will be described in more detail below, in embodiments where the moisturizing lotion composition is used to enhance the antimicrobial efficacy of one or more secondary compounds applied to the skin, panthenol may work together and synergistically with the aloe vera to further sooth skin irritation and further increase the antimicrobial efficacy of such secondary compounds.

Embodiments of the moisturizing lotion composition can include one or more cationic polymers such as guar gum, guar gum modified with hydroxyalkyl groups, guar gum modified with hydroxypropyl groups, or combinations thereof. Guar gum is commercially available as Jaguar® available from Rhodia. The hydroxyalkyl groups may include alkyl groups with any number of carbon atoms. In such embodiments, the cationic polymer(s) (e.g., guar gum) have a concentration (expressed as a wt % of the moisturizing lotion composition) ranging from about 0.17 wt % to about 0.70 wt %, alternatively ranging from about 0.26 wt % to about 0.53 wt %, and alternatively ranging from about 0.31 wt % to about 0.44 wt %. Such cationic polymers offer the potential to provide protection against disruptions of the cell surface by surfactants.

Embodiments of the moisturizing lotion composition can include one or more film forming barriers such as jojoba oil. In such embodiments, the jojoba oil has a concentration (expressed as a wt % of the moisturizing lotion composition) ranging from about 0.05 wt % to about 0.20 wt %, alternatively ranging from about 0.07 wt % to about 0.15 wt %, and alternatively ranging from about 0.09 wt % to about 0.13 wt %. Film barriers such as jojoba oil offer the potential to limit moisture transfer from or through the skin. More particularly, jojoba oil may limit transepidermal water loss from the skin. In addition, jojoba oil may act as an emollient and/or be used to regulate the viscosity of the moisturizing lotion composition.

In some embodiments, the film forming barriers may include argan oil in addition to or as an alternative to jojoba oil. In such embodiments, the argan oil has a concentration (expressed as a wt % of the moisturizing lotion composition) ranging from about 0.02 wt % to about 0.30 wt %, alternatively ranging from about 0.03 wt % to about 0.08 wt %, and alternatively ranging from about 0.04 wt % to about 0.07 wt %.

The one or more film forming layers such as jojoba oil and argan oil form a barrier layer or residue layer adjacent or proximal the skin, while one or more other compounds within the moisturizing lotion composition remain suspended above the skin in an aqueous or semi-aqueous state. Consequently, in embodiments where the moisturizing lotion composition is used to enhance the antimicrobial efficacy of one or more secondary compound(s) applied to the skin, the residue layer may form a physical barrier that reduces contact between the skin and the one or more secondary compound(s). Such buffering offers the potential to reduce irritation of the skin by the secondary compound(s), allow higher concentrations of antimicrobial agents in the secondary compound(s) to be applied to the skin, allow prolonged skin exposure times for the antimicrobial agents in the secondary compound(s), or combinations thereof. The argan oil may also act as an anti-wrinkle agent. Based on some testing, it is believed that argan oil alone or via a synergistic effect when used in combination with chamomilla recutita extract may provide an enhanced analgesic (e.g., pain relieving) benefit.

Embodiments of the moisturizing lotion composition can include an emollient such as butyrospermum parkii (shea butter) or shea butter based esters. In such embodiments, the emollient (e.g., the shea butter or shea butter based esters) has a concentration (expressed as a wt % of the moisturizing lotion composition) ranging from about 0.02 wt % to about 0.10 wt %, alternatively ranging from about 0.03 wt % to about 0.08 wt %, and alternatively ranging from about 0.04 wt % to about 0.07 wt %. A shea butter based ester emollient may be a commercially available product such as SheaLight™ available from Lipex. In some embodiments, the shea butter based ester emollient may be used in combination with other esters, silicone oils, vegetable oils, and synthetic emollients.

Shea butter and shea butter based esters offer the potential to enhance solubility of other compounds in the moisturizing lotion composition, as well as secondary compounds. Without being limited to this or any particular theory, the increased solubility may contribute to a less greasy feel while forming a film barrier along the skin, which may limit transepidermal water loss from the skin. In addition, the increased solubility may provide better mixing with applied secondary compounds, which may facilitate entrapment or suspension of the secondary compounds within a particular volume of the moisturizing lotion compound. Thus, in embodiments where the moisturizing lotion composition is used to enhance the antimicrobial efficacy of one or more secondary compounds applied to the skin, inclusion of shea butter or shea butter based ester may cause the secondary compounds (e.g., hand sanitizer, etc.) to evaporate at a slower rate, thereby extending the period of time the hand sanitizer remains active on the skin.

Embodiments of the moisturizing lotion composition can include a cationic low humidity humectant such hydroxypropyl Bis-hydroxyethyldimonium chloride (Cola° moist 200), which can also aid in moisturizing. In such embodiments, the cationic low humidity humectant (e.g., the hydroxypropyl Bis-hydroxyethyldimonium chloride) has a concentration (expressed as a wt % of the moisturizing lotion composition) ranging from about 1.5 wt % to about 6.0 wt %, alternatively ranging from about 2.3 wt % to about 4.5 wt %, and alternatively ranging from about 2.7 wt % to about 3.8 wt %.

Embodiments of the moisturizing lotion composition can include a willow bark extract such as salix *nigra* willow bark extract. In such embodiments, the willow bark extract (e.g., the salix *nigra* willow bark extract) has a concentration (expressed as a wt % of the moisturizing lotion composition) ranging from about 0.05 wt % to about 0.20 wt %, alternatively ranging from about 0.07 wt % to about 0.15 wt %, and alternatively ranging from about 0.09 wt % to about 0.13 wt %.

Willow bark extract includes salicylic acid, which is an anti-inflammatory agent. Additionally, willow bark extract may provide moisturizing, cleansing, bactericidal, viralcidal, and skin toning benefits. Thus, in embodiments where the moisturizing lotion composition is used to enhance the antimicrobial efficacy of one or more secondary compounds applied to the skin, the salicylic acid in the willow bark extract may work together with the panthenol and the aloe vera to further sooth skin irritation, and further increase the antimicrobial efficacy of such secondary compounds in the manner previously described. In addition, the willow bark extract may increase the antimicrobial properties of the moisturizing lotion composition without the addition or use of a secondary compound. Still further, the willow bark extract offers potential analgesic (e.g., pain relieving) benefits alone and when used in combination with one or more secondary compounds as disclosed herein.

Embodiments of the moisturizing lotion composition can include an alpha hydroxyl acid such as citric acid. In such embodiments, the alpha hydroxyl acid (e.g., the citric acid) has a concentration (expressed as a wt % of the moisturizing lotion composition) ranging from about 0.05 wt % to about 0.20 wt %, alternatively ranging from about 0.07 wt % to about 0.15 wt %, and alternatively ranging from about 0.09 wt % to about 0.13 wt %. The alpha hydroxyl acid can be used to adjust the PH of the moisturizing lotion composition, and further, can be used as a chelating agent to bind metals within the composition and enhance the solubility of the metals. Citric acid also offers the potential to promote skin exfoliation and regeneration.

Embodiments of the moisturizing lotion composition can include lipids or monoglycerides such as glyceryl stearate. In such embodiments, the lipids or monoglycerides (e.g., the glyceryl stearate) has at a concentration (expressed as a wt % of the moisturizing lotion composition) ranging from about 0.25 wt % to about 1.00 wt %, alternatively ranging from about 0.37 wt % to about 0.75 wt %, and alternatively ranging from about 0.45 wt % to about 0.63 wt %. In some embodiments, the lipids or monoglycerides comprises Glyceryl Stearate SE, which is self-emulsifying and contains sodium stearate and/or potassium stearate. In some embodiments, Glyceryl Stearate SE may also be used as a surfactant to enhance mixing of the moisturizing lotion composition and one or more secondary compounds added to the skin (e.g., alcohol, ethanol, vinegar, bleach, or hand sanitizer), thereby providing enhanced dispersion of secondary compounds (e.g., antimicrobial agents) throughout an applied film layer.

Embodiments of the moisturizing lotion composition can include one or more anti-oxidant agent. Examples of suitable anti-oxidant agents include, without limitation, Vitamin A, Vitamin C, Vitamin D, Vitamin E, Vitamin E tocopherol acetate beta-carotene, selenium, and zinc. In such embodiments, the antioxidants have a concentration (expressed as a wt % of the moisturizing lotion composition) ranging from about 0.01 wt % to about 5 wt %.

Embodiments of the moisturizing lotion composition can include one or more antimicrobial compounds with antifungal and/or antibacterial properties. Examples of suitable compounds with antifungal and/or antibacterial properties include Germall® Plus and Liquid Germall® Plus, each of which includes preservative diazolidinyl urea and iodopropynyl butylcarbamate in propylene glycol. In such embodiments, the Liquid Germall® Plus has a concentration (expressed as a wt % of the moisturizing lotion composition) ranging from about 0.15 wt % to about 0.60 wt %, alternatively ranging from about 0.22 wt % to about 0.45 wt %, and alternatively ranging from about 0.27 wt % to about 0.38 wt %. The Liquid Germall® Plus provides diazolidinyl urea at a concentration (expressed as a wt % of the moisturizing lotion composition) ranging from about 0.14 wt % to about 0.55 wt %, and provides iodopropynyl butylcarbamate at a concentration (expressed as a wt % of the moisturizing lotion composition) ranging from about 0.01 wt % to about 0.05 wt %. Thus, in some embodiments, the moisturizing lotion composition may itself exhibit some antimicrobial properties without the addition of a secondary compound (e.g., alcohol, ethanol, vinegar, bleach, hand sanitizer, etc.).

Embodiments of the moisturizing lotion composition can include a long chain organic alcohol such as cetyl alcohol. In such embodiments, the long chain organic alcohol (e.g., cetyl alcohol) has a concentration (expressed as a wt % of the moisturizing lotion composition) ranging from about 0.25 wt % to about 1.00 wt %, alternatively ranging from about 0.37 wt % to about 0.75 wt %, and alternatively ranging from about 0.45 wt % to about 0.63 wt %. A long chain organic alcohol such as cetyl alcohol provides emulsion stabilization, viscosity control, and antimicrobial properties.

Embodiments of the moisturizing lotion composition can include one or more surfactants and emulsion agents such as polysorbate-20. In such embodiments, the surfactant(s) and emulsion agent(s) (e.g., the polysorbate-20) has a concentration (expressed as a wt % of the moisturizing lotion composition) ranging from about 0.25 wt % to about 1.00 wt %, alternatively ranging from about 0.37 wt % to about 0.75 wt %, and alternatively ranging from about 0.45 wt % to about 0.63 wt %. The surfactants and emulsion agents reduce the surface tension between the moisturizing lotion composition and any secondary compounds added to the skin (e.g., alcohol, ethanol, vinegar, bleach, hand sanitizer, etc.), thereby allowing more complete mixing therebetween and enhanced dispersion of antimicrobial agents throughout an applied film layer.

As previously described, the ingredients of the moisturizing lotion composition are mixed in a solvent, and in particular water, to form an aqueous solution. In general, the water can be deionized water, distilled water, or combinations thereof. In some embodiments, water is in the form of a water-based gel or foam. In embodiments described herein, the water generally defines the balance of the moisturizing lotion composition. In particular, the water has a concentration (expressed as a wt % of the moisturizing lotion composition) ranging from about 30 wt % to about 90 wt %, alternatively ranging from about 40 wt % to about 85 wt %, and alternatively ranging from about 58 wt % to about 80 wt %.

The moisturizing lotion composition can also include one or more preservatives. Examples of suitable preservatives include Liquid Germall™ Plus, which can also function as an antimicrobial as previously described. In such embodiments, the preservative(s) has a concentration (expressed as a wt % of the moisturizing lotion composition) ranging from about 0.01 wt % to about 4.0 wt %, and alternatively from 0.10 wt % to about 1.5 wt %. In general, the preservative(s) aid in stabilizing the moisturizing lotion composition.

In general, embodiments of moisturizing lotion compositions disclosed herein can be applied in a variety of suitable manners and to treat a variety of conditions and symptoms. For example, embodiments of the moisturizing lotion composition can be dispensed by an atomizer, pump spray, or propellant based fluid, gel, or foam dispenser. In addition, the moisturizing lotion compositions can be applied to the face (e.g., prior to make-up application) to hydrate the skin, prevent pore clogging, treat acne, or reduce inflammation from acne on the face. Similarly, the moisturizing lotion compositions can be applied other parts of the body (e.g., the trunk) for the foregoing benefits. Further, moisturizing lotion compositions can be used as a skin pre-treatment for application to the skin prior to applying a subsequent medical treatment and/or compound thereto. Without being limited by this or any particular theory, the hydration of the skin by embodiments of moisturizing lotion compositions disclosed herein may act to make the skin more permeable to dermal or transdermal medical applications following the use of the moisturizing lotion composition. For example, the moisturizing lotion compositions can be applied concurrently (e.g., mixed with) other medical compounds, thereby acting directly as a dermal or transdermal delivery agent.

Two or more of the compounds in embodiments of moisturizing lotion compositions described herein may work together to produce beneficial synergistic effects. Without being limited by this or any particular theory, it is believed such synergistic effects may depend on or result from the relative concentrations of such two or more compounds. More specifically, in embodiments of moisturizing lotion compositions disclosed herein, the ratio of the concentration of aloe vera in the moisturizing lotion composition to the concentration of vervain extract in the moisturizing lotion composition ranges from 0.80 to 1.20, alternatively ranges from 0.90 to 1.10, alternatively ranges from 0.95 to 1.05, and alternatively is 1.0. In addition, in embodiments of moisturizing lotion compositions disclosed herein including propylene glycol and panthenol, the ratio of the concentration of propylene glycol in the moisturizing lotion composition to the concentration of panthenol in the moisturizing lotion composition ranges from 40.0 to 60.0, alternatively ranges from 45.0 to 55.0, and alternatively is 50.0. Further, in embodiments of moisturizing lotion compositions disclosed herein including panthenol and chamomilla recutita extract, the ratio of the concentration of panthenol in the moisturizing lotion composition to the concentration of chamomilla recutita extract in the moisturizing lotion composition ranges from 3.0 to 7.0, alternatively ranges from 4.0 to 6.0, alternatively ranges from 4.5 to 5.5, and alternatively is 5.0. Still further, in embodiments of moisturizing lotion compositions disclosed herein including propylene glycol and chamomilla recutita extract, the ratio of the concentration of propylene glycol in the moisturizing lotion composition to the concentration of chamomilla recutita extract in the moisturizing lotion composition ranges from 200.0 to 300.0, alternatively ranges from 225.0 to 275.0, and alternatively is 250.0. In embodiments of moisturizing lotion compositions disclosed herein including chamomilla recutita extract and willow bark extract, the ratio of the concentration of chamomilla recutita extract in the moisturizing lotion composition to the concentration of willow bark extract in the moisturizing lotion composition ranges from 0.80 to 1.20, alternatively ranges from 0.90 to 1.10, alternatively ranges from 0.95 to 1.05, and alternatively is 1.0. And in embodiments of moisturizing lotion compositions disclosed herein including chamomilla recutita extract and argan oil, the ratio of the concentration of chamomilla recutita extract in the moisturizing lotion composition to the concentration of argan oil in the moisturizing lotion composition ranges from 1.0 to 3.0, alternatively ranges from 1.5 to 2.5, alternatively 2.0.

In some embodiments, the moisturizing lotion composition is used on skin to enhance the antimicrobial efficacy of one or more secondary compounds that are also applied to the skin. Such secondary compounds exhibiting antimicrobial properties include, without limitation, hand sanitizer, alcohol, vinegar, bleach (e.g., sodium hypochlorite), mixtures thereof, as well as compounds known in the art as having antimicrobial properties. In some embodiments, a secondary compound includes alcohol (e.g., isopropyl alcohol, ethanol, ethyl alcohol, etc.) having a concentration (expressed as a wt % of the secondary compound) ranging from about 40 wt % to about 100 wt %, alternatively from about 50 wt % to about 90 wt %, and alternatively from about 60 wt % to about 80 wt %. In some embodiments, a secondary compound includes vinegar at a concentration (expressed as a wt % of the secondary compound) ranging from about 0.5 wt % to about 50 wt %, alternatively from about 2 wt % to about 70 wt %, and alternatively from about 5 wt % to about 100 wt %. In some embodiments, a secondary compound includes bleach at a concentration (expressed as a wt % of the secondary compound) ranging from about 0.5 wt % to about 5 wt %, alternatively from about 5 wt % to about 60 wt %, and alternatively from about 10 wt % to about 100 wt %.

In embodiments where the moisturizing lotion composition is used to enhance the antimicrobial efficacy of one or more secondary compounds applied to the skin, the moisturizing lotion composition can be applied to the skin before the secondary compound(s) to form an initial base layer. The base layer may then be allowed to dry on the skin. For example, the base layer may be allowed to dry for a period of time ranging from about 5 seconds to 1 minute, alternatively 15 seconds to about 5 minutes, and alternatively from about 30 seconds to 10 minutes. In other embodiments, no base layer drying time is provided. After the application of the moisturizing lotion composition as a base layer, one or more secondary compounds may be applied to the skin. Without being limited by this or any particular theory, the moisturizing lotion composition protects the skin (e.g., forms a physical barrier) and/or enhances the resistance of the skin to the potentially negative impacts associated with the secondary compounds such as inflammation of the skin, irritation, and drying of the skin. Further, the moisturizing lotion composition may extend the period of time the secondary compound is effective for antimicrobial uses. For example, alcohol contained within hand sanitizer may evaporate at a slower rate when at least partially mixed with moisturizing lotion compositions described herein.

In other embodiments, the one or more secondary compounds are applied before application of the moisturizing lotion composition, the one or more secondary compounds are applied concurrently with the moisturizing lotion composition, or a combination thereof (before and during application of the moisturizing lotion composition). In still other embodiments, the one or more secondary compounds may be provided premixed with the moisturizing lotion composition. In addition, as previously described, some embodiments of the moisturizing lotion composition described herein exhibit antimicrobial properties without the addition or use of a secondary compound.

Embodiments of the moisturizing lotion composition described herein can be used in connection with a lavage procedure in which the one or more secondary compounds are employed as an aqueous flush solution. For example, the moisturizing lotion composition may be applied to the nasal tissues, and a lavage solution including the one or more secondary compounds such as vinegar and/or alcohol may be used to flush particles from the nasal tissues.

To further illustrate various illustrative embodiments of the present disclosure, the following non-limiting examples are provided.

EXAMPLE 1

As previously described, embodiments of moisturizing lotion compositions disclosed herein include one or more of the following: skin conditioning agent(s), aloe vera, algae extract, vervain extract, an anti-inflammatory agent, cationic polymer(s), film forming barrier(s), emollient(s), cationic low humidity humectant(s), willow bark extract, antifungal and/or antibacterial compound(s), cetyl alcohol, surfactant(s) and/or emulsion agent(s), anti-wrinkle agent(s), skin conditioning agent(s), alpha hydroxyl acid(s), lipid(s) and/or monoglyceride(s), and anti-oxidant agent(s). The formulation of one exemplary embodiment of a moisturizing lotion composition in accordance with the principles described herein is provided in Table 1 below.

TABLE 1

| Ingredients | wt % (of the composition) |
|---|---|
| Deionized water | 64.25 |
| Propylene glycol | 25.00 |
| Cola ® moist 200 | 3.00 |
| Algae extract | 2.00 |
| *Aloe vera* | 1.00 |
| Vervain extract | 1.00 |
| Fragrance oil | 0.60 |
| Cetyl Alcohol | 0.50 |
| Glyceryl Stearate SE | 0.50 |
| Panthenol | 0.50 |
| Polysorbate-20 | 0.50 |
| Jaguar HP-8 | 0.35 |
| Liquid Germall ® plus | 0.30 |
| *Chamomilla recutita* extract | 0.10 |
| Citric acid | 0.10 |
| Jojoba oil | 0.10 |
| Willow bark extract | 0.10 |
| Argan oil | 0.05 |
| Lipex SheaLight ™ | 0.05 |
| Total | 100 |

EXAMPLE 2

Embodiments of moisturizing lotion compositions disclosed herein were used to treat skin conditions including eczema, herpes zoster, fibromyalgia, neuropathy, and pain in human patients over a period of time. The symptoms experienced by each patient were identified, and the effectiveness of the treatments based on patient feedback were tracked on a weekly basis. The patients rated the effectiveness of the treatments on a scale—Effective ("E"), Somewhat Effective ("S"), Neutral ("N"), or Ineffective ("I") (listed in order of decreasing effectiveness with Effective being the highest degree of effectiveness and Ineffective being the lowest degree of effectiveness). In cases where the patient previously employed a different therapy to treat the symptom, the effectiveness of the treatments with the moisturizing lotion compositions disclosed herein was evaluated in comparison to the previously employed therapy. In other words, the previously employed therapy served as a baseline against which the effectiveness of treatments with the moisturizing lotion compositions disclosed herein were compared. The results of the treatments are summarized in Table 2 below.

As shown in Table 2 below, each patient treated indicated Effective treatment of the condition and associated symptoms was experienced, and in particular, indicated Effective treatment was experienced relatively quickly or immediately within the first week of treatment. In addition, all but one of the patients treated (Patient No. 15) indicated the treatments were Effective over the entire duration of the treatments. For example, Patient Nos. 1, 4, 5, 8, 13, and 14 indicated treatments were Effective over a period of at least 8 weeks. Although it is not explicitly shown in Table 1, each patient listed in Table 1 indicated onset of benefit(s) (e.g., pain relief) within five (5) minutes of application of the moisturizing lotion composition, and further, each patient listed in Table 1 indicated such benefits lasted at least 7 hours after application, and more generally between 7 and 72 hours after application depending on the particular condition and level of pain. In addition, although it is not explicitly shown in Table 1, patient number 7 indicated complete healing of radiation burns following two weeks of treatments with the moisturizing lotion composition, which is significantly less than the period of time typically expected to fully heal radiation burns via conventional treatments with steroid creams (about four months), which at least suggests the moisturizing lotion composition improved rate of healing of the radiation burn by as much as eight times (8×) as compared to a conventional treatment.

| Patient | | | Symptoms | | | | | | Weeks of Application | | | | Previous Therapies |
|---|---|---|---|---|---|---|---|---|---|---|---|---|---|
| No. | Age | Condition | Dryness | Itching | Swelling | Redness | Pain | Tingling | Burning | 1 | 2 | 4 | 8 | |
| 1 | 46 | Eczema | | x | | | x | | x | E | E | E | E | Eucrisa |
| 2 | 56 | Eczema | x | x | x | | | | | E | E | | | Clobetasol, Prednisone, Triamcinolone |
| 3 | 87 | Eczema, Herpes zoster | | x | | | x | | | E | | | | 0.25% Dexamethasone cream |
| 4 | | Herpes zoster | | | | | x | x | | E | E | E | E | Valtrex |
| 5 | 63 | Fibromyalgia | | | | | x | | | E | E | E | E | |
| 6 | 62 | Irritated legs | | x | | | | x | | E | E | | | N/A |
| 7 | | Radiation burn | | x | | x | x | | | E | E | E | | Vaseline |
| 8 | 57 | Neuropathy | | | | | x | x | | E | E | E | E | Gabapentin |
| 9 | 85 | Neuropathy | | | | | x | x | | E | E | | | |
| 10 | | Neuropathy, Pain in neck and temples | | | | | x | | | E | | | | Gabapentin |
| 11 | 64 | Pain in body | | | | | x | | | E | E | | | N/A |

-continued

| Patient No. | Age | Condition | Symptoms | | | | | | | Weeks of Application | | | | Previous Therapies |
|---|---|---|---|---|---|---|---|---|---|---|---|---|---|---|
| | | | Dryness | Itching | Swelling | Redness | Pain | Tingling | Burning | 1 | 2 | 4 | 8 | |
| 12 | | Pain in both legs and feet | | | | | x | | | E | | | | |
| 13 | 38 | Pain in jaw and tooth | | | x | | x | | | E | E | E | E | BC powder |
| 14 | 62 | Pain in right leg | | | | | x | | | E | E | E | E | N/A |
| 15 | | Pain siatic | | | | | x | | | E | E | S | N | CBD oil |

E = Effective
S = Somewhat Effective
N = Neutral
I = Ineffective

While exemplary embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the disclosure. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A moisturizing lotion composition, comprising:
   water;
   propylene glycol having a concentration of 21.0 to 37.5 wt % of the moisturizing lotion composition;
   aloe vera having a concentration of 0.50 to 4.0 wt % of the moisturizing lotion composition;
   vervain extract having a concentration of 0.50 to 4.0 wt % of the moisturizing lotion composition;
   willow bark extract having a concentration of 0.50 to 0.20 wt % of the moisturizing lotion composition; and
   chamomilla recutita extract having a concentration of 0.05 to 0.40 wt % of the moisturizing lotion composition;
   wherein a ratio of the concentration of the aloe vera to the concentration of the vervain extract is between 0.90 and 1.10.

2. The moisturizing lotion composition of claim 1, further comprising:
   argan oil having a concentration of 0.02 to 0.30 wt % of the moisturizing lotion composition.

3. The moisturizing lotion composition of claim 2, further comprising:
   an algae extract having a concentration of 1.5 to 3.0 wt % of the moisturizing lotion composition.

4. The moisturizing lotion composition of claim 2, further comprising:
   panthenol having a concentration of 0.25 to 2.0 wt % of the moisturizing lotion composition.

5. The moisturizing lotion composition of claim 1, wherein the water is de-ionized water having a concentration of 40 to 85 wt % of the moisturizing lotion composition.

6. The moisturizing lotion composition of claim 1, wherein the concentration of the propylene glycol is 22.5 wt % to 31.3 wt %.

7. The moisturizing lotion composition of claim 1, wherein the concentration of the aloe vera is 0.9 to 1.25 wt %.

8. The moisturizing lotion composition of claim 1, wherein the concentration of the chamomilla recutita extract is 0.09 to 0.13 wt % of the moisturizing lotion composition.

9. The moisturizing lotion composition of claim 1, wherein a ratio of the concentration of the propylene glycol to the concentration of the chamomilla recutita extract is between 4.5 and 5.5.

10. The moisturizing lotion composition of claim 1, further comprising a secondary compound including alcohol having a concentration of 40 to 100 wt % of the secondary compound.

11. A moisturizing lotion composition, comprising:
    de-ionized water;
    propylene glycol having a concentration of 12.5 to 50.0 wt % of the moisturizing lotion composition;
    aloe vera having a concentration of 0.5 to 2.0 wt % of the moisturizing lotion composition;
    vervain extract having a concentration of 0.50 to 4.0 wt % of the moisturizing lotion composition;
    chamomilla recutita extract having a concentration of 0.07 to 1.5 wt % of the moisturizing lotion composition; and
    panthenol having a concentration of 0.25 to 2.0 wt % of the moisturizing lotion composition; and
    willow bark extract having a concentration of 0.09 to 0.13 wt % of the moisturizing lotion composition;
    wherein a ratio of the concentration of the aloe vera to the concentration of the vervain extract is between 0.90 and 1.10;
    wherein a ratio of the concentration of the propylene glyocol to the concentration of the panthenol is between 45.0 and 55.0.

12. The moisturizing lotion composition of claim 11, further comprising an antimicrobial compound.

13. The moisturizing lotion composition of claim 12, wherein the antimicrobial compound comprises:
    diazolidinyl urea having a concentration of 0.14 to 0.55 wt % of the moisturizing lotion composition; or
    iodopropynyl butylcarbamate having a concentration 0.01 to 0.05 wt % of the moisturizing lotion composition.

14. The moisturizing lotion composition of claim 11, further comprising a secondary compound including alcohol having a concentration of 40 to 100 wt % of the secondary compound.

15. The moisturizing lotion composition of claim 11, wherein a ratio of the concentration of the chamomilla recutita extract to the concentration of the willow bark extract is between 0.80 and 1.20.

16. The moisturizing lotion composition of claim 15, further comprising argan oil having a concentration of 0.04 to 0.07 wt % of the moisturizing lotion composition, wherein a ratio of the concentration of the chamomilla recutita extract to the concentration of the argan oil is between 1.5 and 2.5.

17. The moiusturizing lotion composition of claim 11, wherein a ratio of the concentration of the panthenol to the concentration of the chamomilla recutita extract is between 4.0 and 6.0.

18. A moisturizing lotion composition, comprising:
water;
propylene glycol having a concentration of 21.0 to 37.5 wt % of the moisturizing lotion composition;
aloe vera having a concentration of 0.50 to 4.0 wt % of the moisturizing lotion composition;
vervain extract having a concentration of 0.50 to 4.0 wt % of the moisturizing lotion composition;
willow bark extract having a concentration of 0.50 to 0.20 wt % of the moisturizing lotion composition;
chamomilla recutita extract having a concentration of 0.05 to 0.40 wt % of the moisturizing lotion composition; and
one or more cationic polymers having a concentration of 0.17 to 0.70 wt % of the moisturizing lotion composition;
wherein a ratio of the concentration of the aloe vera to the concentration of the vervain extract is between 0.90 and 1.10.

19. The moisturizing lotion composition of claim 18, wherein the one or more cationic polymers comprises guar gum.

20. The moisturizing lotion composition of claim 18, further comprising:
jojoba oil having a concentration of 0.05 to 0.20 wt % of the moisturizing lotion composition.

21. The moisturizing lotion composition of claim 18, further comprising:
an emollient having a concentration of 0.02 to 0.10 wt % of the moisturizing lotion composition.

22. The moisturizing lotion composition of claim 18, further comprising:
an algae extract having a concentration of 1.5 to 3.0 wt % of the moisturizing lotion composition; and
panthenol having a concentration of 0.25 to 2.0 wt % of the moisturizing lotion composition.

* * * * *